United States Patent

Kim et al.

Patent Number: 5,514,175
Date of Patent: May 7, 1996

[54] AURICULAR ELECTRICAL STIMULATOR

[75] Inventors: Ki Ho Kim, West Orange; Saul Liss; Bernard Liss, both of Paterson, all of N.J.

[73] Assignee: Cerebral Stimulation, Inc., Paterson, N.J.

[21] Appl. No.: 336,762

[22] Filed: Nov. 9, 1994

[51] Int. Cl.$^6$ .............................. A61N 1/00; A61N 1/36; A61H 39/04

[52] U.S. Cl. .............. 607/136; 607/115; 607/57; 607/58

[58] Field of Search ................. 607/2, 4, 5, 55, 607/58, 118, 123, 136, 137, 115, 46, 72, 73, 74; 128/734, 741

[56] References Cited

U.S. PATENT DOCUMENTS

| | | | |
|---|---|---|---|
| 4,267,838 | 5/1981 | McCall | 607/136 |
| 4,305,402 | 12/1981 | Katims | 607/58 |
| 4,319,584 | 3/1982 | McCall | 607/136 |
| 4,450,846 | 5/1984 | McCall | 607/136 |
| 4,966,164 | 10/1990 | Colsen et al. | 607/136 |
| 4,989,605 | 2/1991 | Rossen | 607/55 |

FOREIGN PATENT DOCUMENTS

| | | | |
|---|---|---|---|
| 2361917 | 8/1976 | France | 607/2 |
| 676287 | 3/1976 | U.S.S.R. | 607/55 |
| 1560208 | 1/1987 | U.S.S.R. | 607/58 |

Primary Examiner—Angela D. Sykes
Assistant Examiner—Stephen Huang
Attorney, Agent, or Firm—Hopgood, Calimafde, Kalil & Judlowe

[57] ABSTRACT

Described is a low voltage, multipoint auricular stimulator which is lightweight, portable and unobtrusive for use by a patient to reduce or eliminate sensations of pain and anxiety and for correcting other neural dysfunctions, and a treatment method incorporating the pain reducing and neural dysfunction correcting apparatus.

7 Claims, 3 Drawing Sheets

AURICULAR ELECTRICAL STIMULATOR

FIELD OF THE INVENTION

The invention relates to non-chemical alleviators of pain. More particularly, the invention is an apparatus for reducing pain and correcting other neurally related dysfunctions using a low voltage electric circuit, and a treatment method which incorporates the pain reducing and neural dysfunction correcting apparatus.

BACKGROUND OF THE RELATED ART

Sensations of pain and associated feelings of anxiety can be attributed to numerous physiological and psychological dysfunctions. Pain and anxiety can be adaptive neurological sensations which perform a protective function by warning the individual of possible biological threat or harm from the environment.

There exist also neurologically originated sensations of pain and anxiety which do not perform adaptive warning functions. For example, the withdrawal period from chemical dependence, alcoholism and habitual smoking are characterized by significant pain and anxiety as the body attempts to return its endogenous neural transmitter levels back to homeostasis. Other conditions which are sometimes characterized by periodic, neurologically dependent pain and anxiety of this type include obesity, dieting, impotency, depression, temporo-mandibular-joint (TMJ) syndrome and migraine headache.

The most common method of treating pain and anxiety is pharmacological, through use of bioactive chemical agents such as narcotics, sedatives and analgesics. The problem with chemical therapy is its non-specific, generalized nature which results in numerous side effects. Drawbacks to repeated and continuous drug ingestion or infusion include toxicity, allergic reactions and chemical dependence.

In view of the problems associated with pharmacological treatments, efforts have been made to discover non-chemical approaches to alleviate pain and anxiety. One approach is the use of bipolar, electrical stimulators such as disclosed in U.S. Pat. No. 5,109,847 issued to Saul Liss et al., the teachings of which are incorporated by reference herein. Such electric stimulators alter the levels of neurotransmitters such as ACTH, cortisol, dopamine, beta-endorphins, GABA and serotonin, which are associated with transmission of pain sensations and other neurophysiological functions.

Certain types of pain or anxiety can be effectively modulated by non-chemically altering the transmission of electrical signals relating to perceptions of pain or anxiety between specific nodes of a particular neurological pathway. Many such specific pathways and nodes have been anatomically mapped and are known to be distributed throughout an individual's body. These pathways can transmit signals and corresponding neural responses such as those associated with pain or those which perform control functions such as signals from the viscera indicating a hunger sensation.

One example of such a network of nodes are those located on or proximate the ear referred to herein as the auricular plexus or known otherwise in the art as auricular points. Specific forms of pain or anxiety are effectively modulated by transmission of electrical signals along the network of nodes associated with the auricular plexus.

Multiple auricular points are associated with the tenth and longest cranial nerve (also called the vagus nerve) which anatomically connects through the neck, thorax and abdominal regions, and extends upward into the cervical region and downward into the larynx and pharynx supplying sensations from these regions to the central nervous system. The vagus nerve also supplies motor signals to the vocal chord muscles, and motor and secretory impulses to the abdominal and thoracic viscera.

Surprisingly, dysfunctions such as continuous urges to eat, smoke or drink alcohol, impotency or unexplained depressions can all be improved through introduction of electrical signals along the neurological pathways associated with auricular points, as will be described in detail hereinbelow. These empirical observations have led to the conclusion that maladaptive behaviours such as obesity, inability to maintain a controlled diet, impotency and depression may all have, in part, an etiology related to dysfunction of neural pathways.

There is a need in the art for an effective, non-chemical method and apparatus for preventing messages related to pain or anxiety from flowing between specific nodes of a particular neurological pathway such as those associated with the multiple auricular points, and for correcting dysfunctional transmissions of electrical signals along neurological pathways associated with such auricular points.

Currently known electrical devices and methodology are designed with signal generating circuits fed by relatively high voltage supplies (such as between about 27 to about 40 volts) and use relatively larger diameter contacts (about 1.75 inches) resulting in low current density therapy. For application to auricular points, there is a need for an electrical stimulator for ameliorating neural pathway anomalies, which can be operated from a signal generating circuit fed from a relatively low voltage source which provides all of the conveniences associated with the reduced voltage operation.

SUMMARY OF THE INVENTION

The invention may be summarized, at least in part, with reference to its objects, one of which is to provide a low voltage apparatus to therapeutically control sensations of pain, feelings of anxiety and other defects in neural pathways, and a method for treating patients using a portable and unobtrusive embodiment of the low voltage apparatus.

It is another object of the invention to provide a low voltage, lightweight and portable apparatus for use in alleviating pain, anxiety and other neural pathway dysfunctions, which uses at least two auricular points and one external reference point on a patient.

It is yet another object of the invention to simultaneously stimulate with an electric circuit, acupuncture points located on, in or around auricular points on and proximate the ears of a patient for improving neural pathways which cause pain, anxiety and other neural related, maladaptive dysfunctions.

A further object of the present invention is to provide an apparatus and method for selectively controlling defective neural pathways which cause pain, anxiety and other dysfunctions, which pathways are localized by stimulating points located in or around a patient's ears through the use of timed electrical stimulation patterns.

It is still another object of the present invention to provide a method using a portable, unobtrusive, electric signal generating apparatus for attenuating pain and anxiety, and for improving dysfunctional neuronal pathways associated with such chronic ailments as obesity, inability to maintain a diet, habitual smoking, alcohol or substance abuse, impotency, depression, temporo-mandibular-joint (TMJ) syndrome and migraine headaches.

The above and other objects of the present invention are realized in a specific illustrative multipoint, electrical auricular stimulator. This device comprises an adaptation of the cranial stimulator as described in detail in U.S. Pat. No. 5,109,857, and further utilizes miniaturized electronics mounted within a light weight, unobtrusive, portable mechanical package. The preferred mechanical package has a shape similar to that of an over-the-ear hearing aid. This stimulator is connected to an ear contact assembly placed in or on a patient's ear for transmission of electrical stimulation to the auricular points.

Essentially, the portable apparatus for treating dysfunctions in neural pathways by acting upon multiple auricular points, comprises a miniaturized stimuli generating means for generating stimulating treatment signal patterns. The generating means is capable of generating patterns of varying duration. The stimuli transmitting means is placed on at least two auricular points for transmitting the patterns to these points.

The transmitting means is placed on at least two intra-auricular points or two post-auricular points or a combination thereof. The apparatus also may have miniaturized indicating means for indicating various times of transmission of the patterns. The indicating means further comprises audible indicating means for audibly indicating the beginning, termination and interim point or points of the transmission duration patterns.

There is also provided a first connection means for connecting the generating and transmitting means to allow the patterns to pass from the generating means to the transmitting means. A miniaturized control means for controlling the generation and duration of the patterns is included on the device and a reference terminal is placed on a reference point and electrically connected to the generating means. The reference terminal may be adhesively placed on the mastoid process.

The generating means generates treatment signal patterns having durations from less than 1 minute up to 60 minutes or more, and generates bipolar signals having, for example but not limited to, frequencies of 15 hz, 500 hz, and 15,000 hz.

In an alternate embodiment, referred to herein as the "professional model" the above-described device is further comprised of an impedance or resistance detector circuit. Using a sensing probe connected to the circuit, a physician or an operator is able to locate points of low impedance or low resistance on the patient's skin.

The invention also comprises a method for modulating neural pathway dysfunctions using the portable apparatus defined above and the first step includes finding auricular points to be stimulated in or around a person's ears. The dysfunctional neural pathways are associated with such auricular points. When using the professional model, the means for locating points of low impedance or low resistance is used to find the stimulation points. In a unit which does not have an integrated low impedance point locating means, the professional uses an independent impedance measuring circuit such as described in U.S. Pat. No. 5,109,857 to locate stimulation points.

The portable apparatus is then positioned on at least one of the person's ears, and at least one circuit reference terminal is placed on a reference point on the external surface of the subject. Care is taken to ensure that at least one of the circuit contact points is placed on at least one of the located auricular stimulation points on the external surface of the subject. Electric power is supplied to the portable apparatus such that a circuit is created from the stimulus generating means located in the apparatus through the circuit contact points, the dysfunctional neural pathways and closes with the reference terminal, whereby therapeutic electric signals are generated in the circuit.

The foregoing features of the present invention may be more fully understood in view of a specific illustrative embodiment described below in conjunction with the following drawings of which:

DESCRIPTION OF THE ILLUSTRATIVE EMBODIMENT

Figure 1:
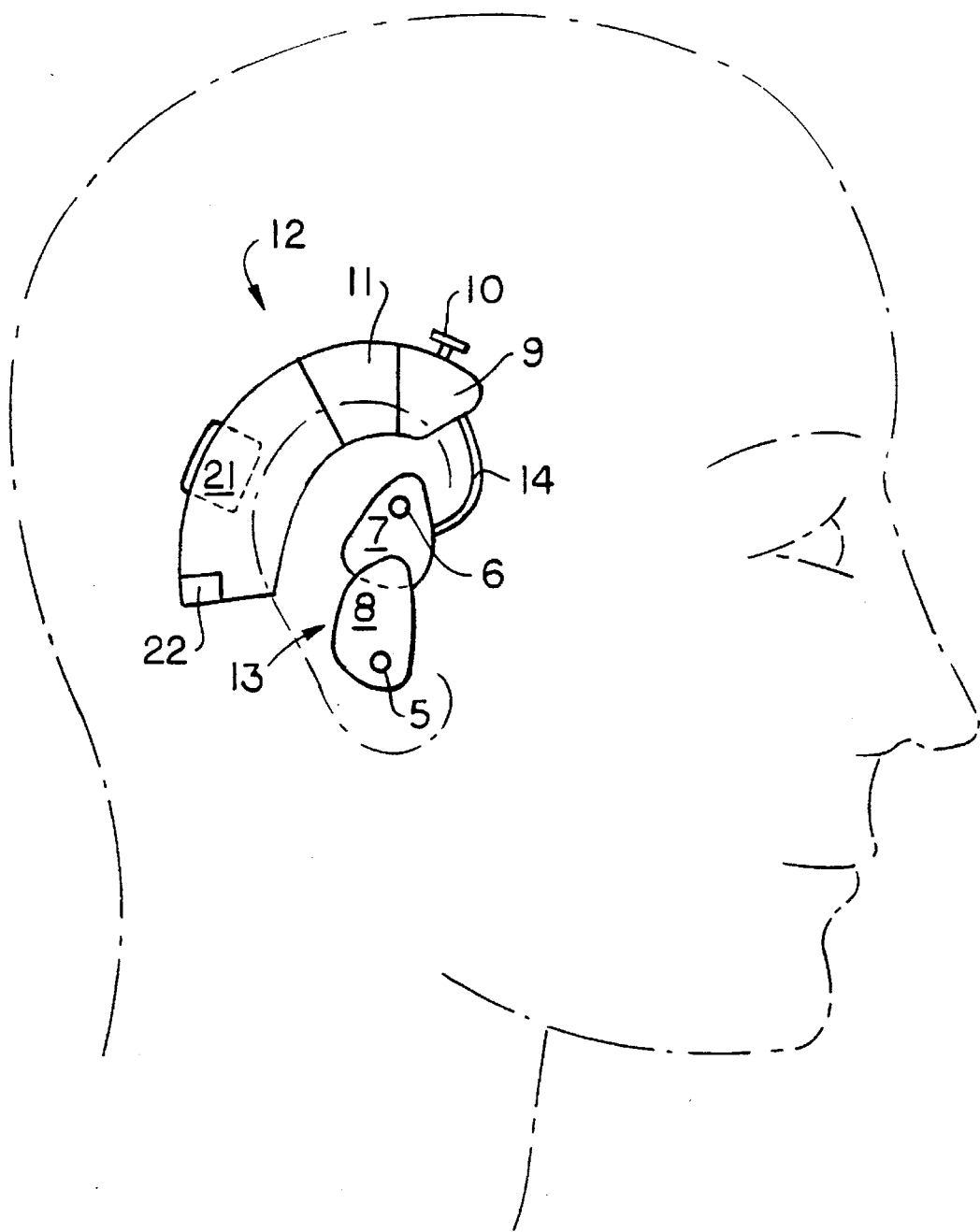
FIG. 1 is an illustrative sketch depicting the arrangement of the inventive stimulator on a patient's ear.

Referring first to FIG. 1, there is shown an illustrative embodiment of the invention. Specifically, inside an electronics package generally designated with numeral 12, is disposed a stimuli generating means 11 which is connected to ear contact assembly 13. Ear contact assembly 13 is a stimuli transmitting means which is connected to stimuli generating means 11 via a first connecting means 14. Connecting means 14 may be a conductive wire or any other means for allowing electrical signal patterns generated by stimuli generating means 11 to be passed through to ear contact assembly 13.

Electronics package 12 is placed over the ear of the patient (depicted in phantom lines) as shown, and ear contact assembly 13 transmits therapeutic electric signals onto a patient's ear. As shown in FIG. 1, ear contact assembly 13 comprises at least two transmission points 5 and 6 which are placed on or over selected intra-auricular nodes or acupuncture points of a patient's ear for transmitting treatment signals to such nodes.

Although FIG. 1 depicts transmission points 5 and 6 localized over intra-auricular nodes, one skilled in the art can readily appreciate alternative possibilities such as locations over post auricular nodes to achieve similar results. In addition, although only two such transmission points are depicted in FIG. 1, the inventive idea encompasses assemblies which have a plurality of transmission points exceeding two with which similar results may be achieved. The number of points used is limited only by practical power requirements of the electronics package, by the number of available nodes to stimulate, and the number of etiologies to be addressed.

FIG. 1 shows that ear contact assembly 13 comprises two connected sections 7 and 8, each section containing at least one transmission point 5 or 6. Sections 7 and 8 are adjustable relative to each other and allow for varying degrees of size in patient ears.

Stimuli generating means 11, housed inside electronics package 12, is comprised of miniaturized electronic circuits which generate electric therapeutically stimulating signals. The signals include low power waveforms such as described in U.S. Pat. No. 5,109,847 to Liss et al. The electronics package may be powered by a suitable DC power source, typically a replaceable battery.

Known electrical devices for signal generating circuits are fed from relatively high voltage multipliers of between about 27 to about 40 volts and consequently require relatively larger contacts usually about 1.75 inches in diameter. For application to auricular points such as proximate to transmission points 5 and 6, electrical stimulator 11 can be operated from a signal generating circuit fed from a relatively low voltage source as low as 2 volts (a 20:1 reduction) and results in the ability to use contacts about 0.093 inches in diameter.

Package 12 also houses control means 9 which comprises a pushbutton 10 for manual initiation of the stimulating signals from generating means 11. Such signals may comprise a pattern of signals applied to points 5 and 6 for selected and adjustable periods of treatment time. For example, such a pattern may be applied to deliver treatment over a duration from about 1 minute up to about 30 minutes, the specific treatment duration being controllable by control means 9 according to the physician's recommended regimen. Such signals may vary in frequency steps, for example but not limited to 15 hz, 500 hz, 15,000 hz and higher steps. The signals are bipolar and have a peak current of about 150 microamps at less than about 10 volts.

Electronics package 12 has attached to it a contact or reference terminal 21 shown in FIG. 1 as being placed on or over the mastoid process. Terminal 21 is preferably comprised of a self adhesive electrode. Reference terminal 21 provides closed circuit connection for electronics package 12 by completing the circuit from generating means 11 through transmission point 5 and 6, through the auricular points and associated neural pathways and back to terminal 21. Although FIG. 1 shows the illustrative terminal 21 as being placed over the mastoid process, one skilled in the art can find alternate anatomical features as may be necessary during treatment.

In order to assist the patient or treating physician in selecting and monitoring a certain treatment period, indicating means 22, which can be an audible signal generator, emits a signal indicating the selected duration. These signals can also indicate that treatment, i.e. stimulation, has begun or ceased. Other signals may indicate selected interim periods, such as every minute or periodically during treatment.

Figure 2:
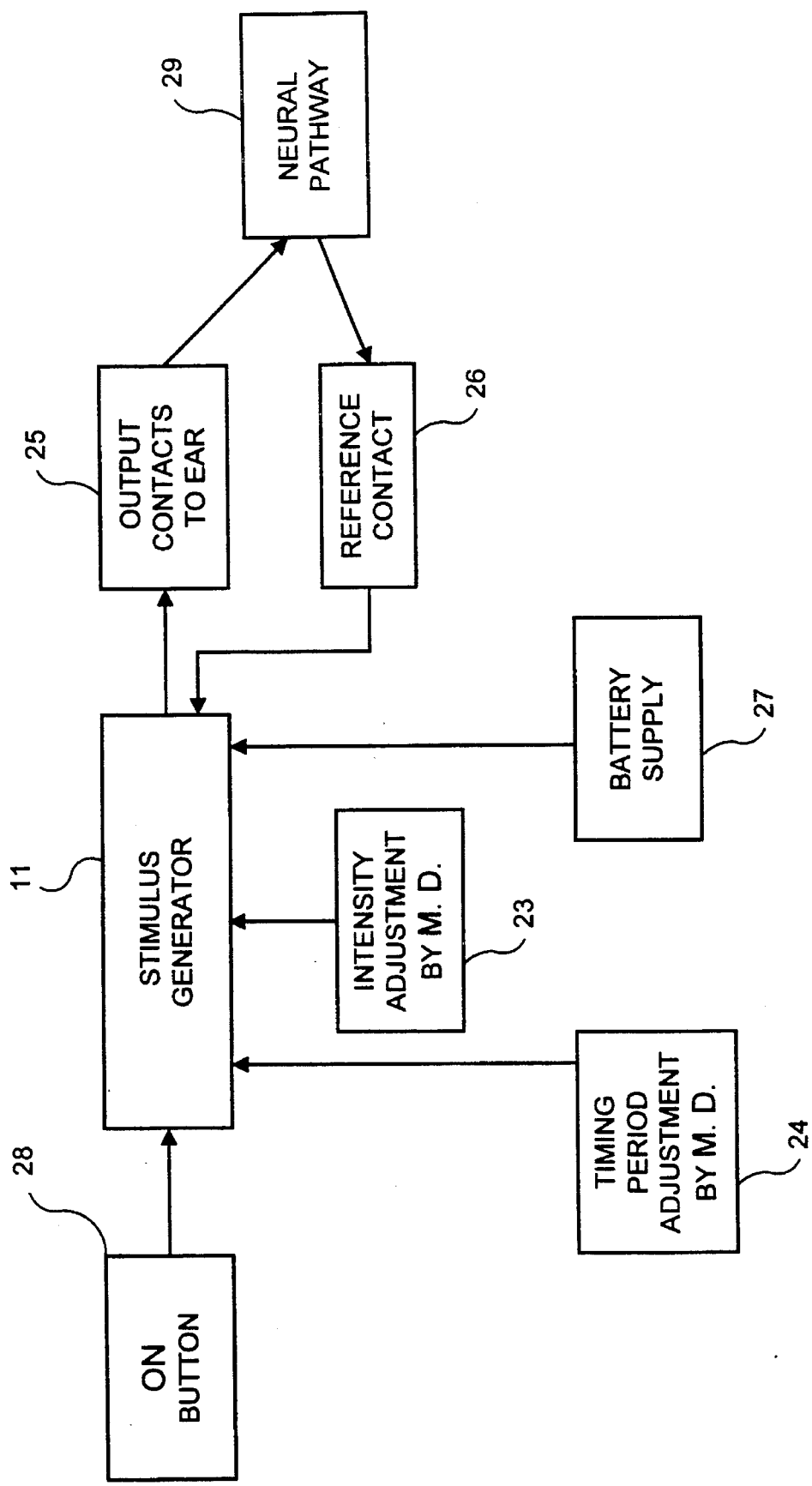
FIG. 2 is a block diagram depicting the preferred method of operation of the inventive stimulator.

Turning now to FIG. 2 there is shown a block diagram outlining the operational features of the invention. It is recommended that therapy employing the apparatus and method be conducted under the supervision of a physician, and following the instructions of a professional the instrument design is of a simplified nature which allows the layperson to use it. By way of example, auricular points to be stimulated are first localized by using an impedance measuring circuit such as described above in the SUMMARY section. The professional uses an impedance measuring circuit to locate points of low impedance or low resistance on the patient's skin which are used for stimulation.

If the professional model is used, the impedance or resistance detector circuit is integrated into the electronics package. In this arrangement, the electronics package has a sensing probe with a tip diameter preferably from about 0.04 inches to about 0.09 inches. The probe is connected to the circuit and the physician is able to locate points of low impedance or low resistance on the patient's skin without using a separate apparatus. In the professional model, the impedance levels are announced by a meter, an LED display, an LCD display or by a change in the pitch of a sonic annunciator.

Numeral 25 in FIG. 2 denotes placement of contact points (such as points 5 and 6 shown in FIG. 1) on the external surface of a patient's ear, preferably in the depressed area of the pinna leading to the ear cavity on a custom-molded ear plug or with an appropriately adjustable ear contact assembly for a snug fit. The electronics package is positioned on the peripheral ridge of the pinna of the subject's ear, and numeral 26 in FIG. 2 denotes the positioning of the reference terminal over the mastoid process to establish the reference contact.

The electronics package is turned on as noted in grid 26 with power supplied by battery as noted in grid 28 which creates a circuit with the stimulus generating means 11 transmitting signals in the circuit through output contacts 25 (transmission point 5 and 6 in FIG. 1) through the auricular points and associated neural pathways 29 and back to reference contact 26 (terminal 21 in FIG. 1). Reference contact 26 can, of course, be on an anatomical feature on the subject other than the mastoid process.

Stimuli generator 11 through miniaturized electronic circuits, generates electric therapeutically stimulating low power waveforms. Such signals comprise a pattern of signals applied to output contacts 25 for selected and adjustable current and periods of treatment time. The physician prescribes the treatment duration according to the requirements of the particular patient and particular malady.

The pattern of treatment signals is adjusted for duration of treatment (timing period adjustment, grid 24) to deliver low power waveforms over set time periods ranging from about 1 minute up to about 60 minutes, the specific treatment duration being controllable by control means 9 shown in FIG. 1.

In FIG. 2, grid 23 notes intensity adjustments. The signals are stepwise adjusted for frequencies, for example but not limited to 15 hz, 500 hz and 15,000 hz. The bipolar signals can be adjusted in the range from about 10 to about 145 microamps at less than about 10 volts depending again on the severity and duration of a patient's condition.

Though the above embodiments of the invention have focused on the stimulation of points on, in or around one ear, both ears may be stimulated simultaneously or in an alternative fashion by placing a second, similar structure as hereinabove described on, in or over the patient's remaining ear. It should be noted, however, that all the elements described as shown in FIGS. 1 and 2 may not be present in, on or over both ears.

Figure 3:
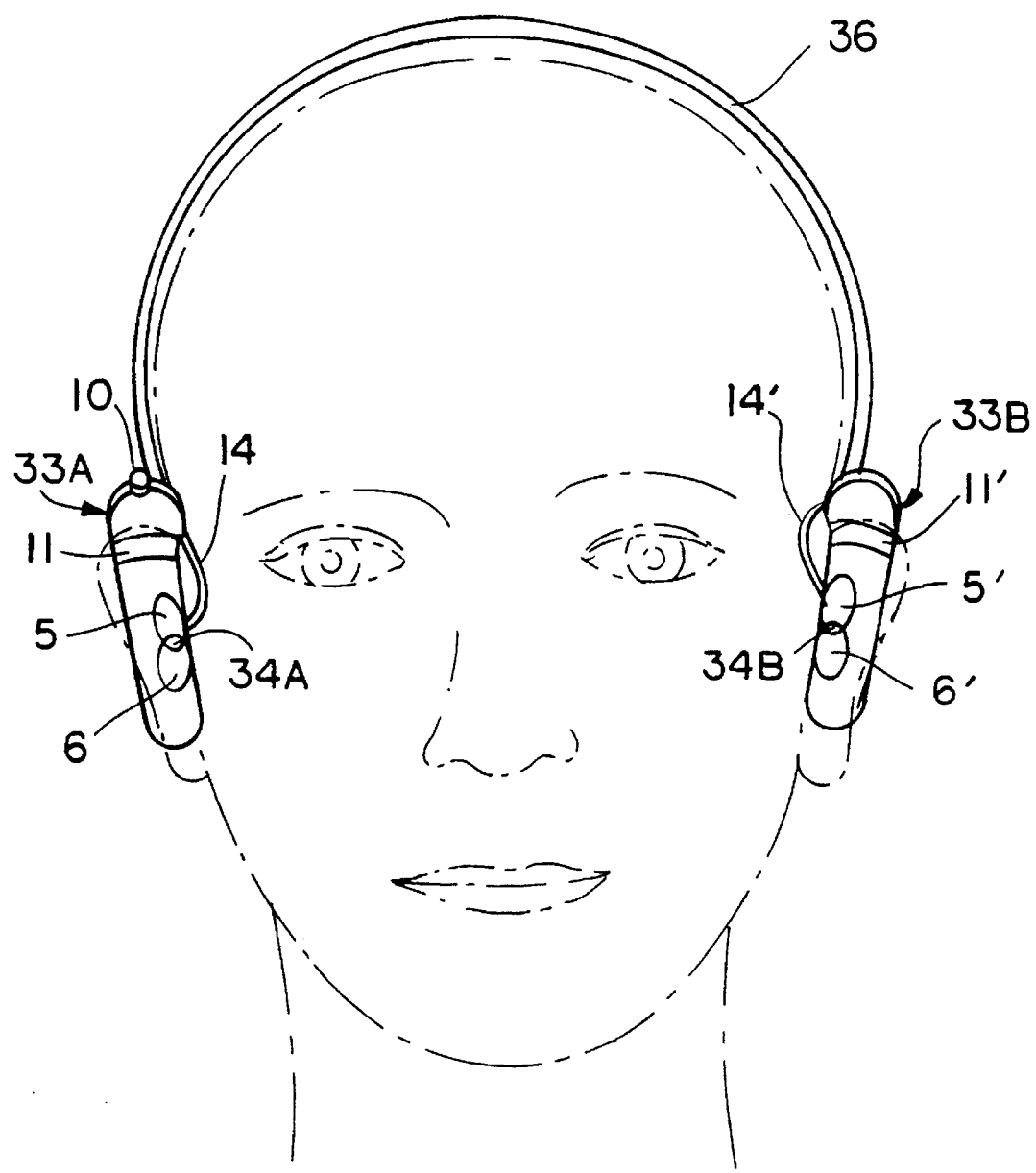
FIG. 3 depicts a patient wearing a pair of inventive stimulators on both ears.

For example, depending on power requirements both master and slave electronics packages 33A and 33B, respectively, shown in FIG. 3 may be powered by a power source located in only one of the two packages. Likewise, one stimuli generating means (either 11 or 11') may be used to generate stimulating signals which are passed to both ear contact assemblies 34A and 34B for stimulation of the auricular points on and around both ears.

Each component of the electronics package 33A or 33B may further comprise its own control means or pushbutton, or have a single pushbutton 10 as depicted in FIG. 3, which controls the operation of both parts of the package. In such a case with only one pushbutton 10 located on part 33A (or a single power supply and stimuli generating means), contact assembly 34B on the second part 33B must be connected to the first package using a headset type connector or second connection means 36.

Such apparatus as described hereinabove is effective in controlling pain, anxiety and maladaptive behaviours such as those found in obesity, inability to maintain a diet, habitual smoking, alcohol or substance abuse, impotency and depression, as shown in the following clinical example.

CLINICAL EXAMPLE

The following table summarizes the specific condition treated, the duration of therapy using the presently disclosed device and the results of the clinical trials.

TABLE I

| Patient | Condition | Duration of therapy | Results |
|---------|-----------|---------------------|---------|
| A | Chronic intractable cervical, upper back and extremity pain and numbness, and associated fibromyalgia | 1 year | 70% relief |
| B | Atlanta-axial tilt with chronic headache, cervical pain, vertigo and nausea | 1 year | total relief of symptoms |
| C | Severe, intractable migraine | 4 weeks | some benefits noted |
| D | Right trigeminal neuralgia with intractable pain in the right side of the face | 7 weeks | moderate relief of symptoms |
| E | Left facial neuralgia cervical pain | 4 weeks | total relief of symptoms |
| F | Overweight and unable to maintain a diet | 3 weeks | appetite and diet under control |
| G | Fibromyalgia with cervical, back and extremity pain | 4 weeks | patient could not tolerate use of device |
| H | Myofacial pain with cervical and back pain | 4 weeks | patient could not tolerate use of device |
| I | Diabetic neuropathy and right sciatica | 4 weeks | patient could not use device |

Patient A with chronic intractable cervical, upper back and extremity pain and numbness also showed symptoms indicating fibromyalgia syndrome. A bilateral unit was adjusted onto both ears of patient A and duration was set at 1 to 2 hours per treatment session. After each auricular cerebral stimulation session the patient was able to obtain moderate relief of pain which lasted several hours. After 1 year of treatment, patient A was assessed to have approximately 70% relief of symptoms. The patient expressed a slight compliance difficulty in physically using the bilateral device which may have contributed to the less than 100% relief.

Upon initial assessment, patient B had an atlanto-axial tilt and complained of chronic headaches, cervical pain, vertigo and nausea. A right ear unit was adjusted onto patient B's ear and she responded well to cerebral stimulation from the beginning with relief of symptoms as early as after the first session. After 1 year of treatment, patient B was assessed to have 100% relief of symptoms.

Patient C had severe, intractable migraine headaches. After 4 weeks of treatment with a right ear unit, some abatement of pain was noted. However, electric treatment was discontinued in favor of chemical therapy as her symptoms were not responding at a dramatic rate to electric stimulus. It was subsequently discovered that patient C's migraine headaches were due to an estrogen imbalance.

Patient D with right trigeminal neuralgia and complaints of an intractable lancinating pain in the right side of her face achieved good pain relief results when a right ear unit was used on an as-needed basis. Patient E with left facial neuralgia and cervical pain achieved total relief after using a left ear unit on an as-needed basis for 4 weeks.

Patient F who was overweight and could not maintain a diet due to an inability to suppress urges for food was able to control her appetite and begin a clinically approved diet of only 1 to 2 meals a day after using a left ear unit for 3 weeks. Patients G, H and I could not adjust to use of the device.

The above embodiments of the invention have been described with reference to specific elements in order to enhance the understanding of the functional characteristics of the system. Numerous substitutes, equivalents and adaptations thereof will be readily apparent to those skilled in the art without departing from the spirit and scope of the present invention.

What we claim is:

1. A portable apparatus for treating dysfunctions in neural pathways by acting upon multiple auricular points, comprising:

miniaturized stimuli generating means for generating stimulating treatment signal patterns, said generating means being capable of generating patterns of varying duration;

stimuli transmitting means adapted to be placed on at least two auricular points for transmitting said patterns to said points;

first connection means for connecting said generating and transmitting means to allow said patterns to pass from said generating means to said transmitting means;

miniaturized control means for controlling generation and duration of said patterns;

a reference terminal placed on a reference point and electrically connected to said generating means; and miniaturized indicating means for indicating various times of transmission of said patterns, wherein said indicating means further comprises audible indicating means for audibly indicating beginning, termination and interim point or points of the transmission duration patterns.

2. The apparatus of claim 1, wherein said generating means generates treatment signal patterns having durations of less than 1 minute up to 60 minutes or more.

3. The apparatus of claim 1, wherein said generating means generates bipolar signals having various discrete frequencies such as 15 hz, 500 hz, and 15,000 hz.

4. The apparatus of claim 1, wherein said transmitting means further comprises two adjustable, connected sections.

5. The apparatus of claim 1, further comprising an impedance or resistance detector circuit integrated into said portable apparatus.

6. The apparatus of claim 5, wherein said impedance or resistance detector circuit further comprises a sensing probe connected to said circuit, said probe having a tip diameter from about 0.04 inches to about 0.09 inches.

7. The apparatus of claim 5, wherein said impedance detector circuit has connected thereto a means for announcing impedance levels selected from the group consisting of a meter, an LED display, an LCD display and a sonic annunciator.

* * * * *